(12) United States Patent
Kindt et al.

(10) Patent No.: US 11,253,702 B2
(45) Date of Patent: Feb. 22, 2022

(54) DEVICE AND METHOD FOR SUPPLYING ENERGY TO AN ACTIVE OCULAR IMPLANT

(71) Applicant: Carl Zeiss AG, Oberkochen (DE)

(72) Inventors: Johannes Kindt, Weimar (DE); Hans-Juergen Dobschal, Kleinromstedt (DE)

(73) Assignee: CARL ZEISS AG, Oberkochen (DE)

( * ) Notice: Subject to any disclaimer, the term of this patent is extended or adjusted under 35 U.S.C. 154(b) by 184 days.

(21) Appl. No.: 16/079,226

(22) PCT Filed: Feb. 20, 2017

(86) PCT No.: PCT/EP2017/053812
§ 371 (c)(1),
(2) Date: Aug. 23, 2018

(87) PCT Pub. No.: WO2017/144421
PCT Pub. Date: Aug. 31, 2017

(65) Prior Publication Data
US 2019/0046798 A1  Feb. 14, 2019

(30) Foreign Application Priority Data

Feb. 24, 2016  (DE) .......................... 102016103285.9

(51) Int. Cl.
| | | |
|---|---|---|
| *A61N 1/00* | (2006.01) | |
| *A61N 1/36* | (2006.01) | |
| *A61N 1/378* | (2006.01) | |
| *A61F 2/14* | (2006.01) | |
| *A61F 9/00* | (2006.01) | |
| *A61F 2/16* | (2006.01) | |
| *A61N 1/05* | (2006.01) | |

(52) U.S. Cl.
CPC ............ *A61N 1/36046* (2013.01); *A61F 2/14* (2013.01); *A61F 9/0017* (2013.01); *A61N 1/3787* (2013.01); *A61B 2560/0219* (2013.01); *A61F 2/16* (2013.01); *A61F 2250/0001* (2013.01); *A61N 1/0543* (2013.01)

(58) Field of Classification Search
CPC .................................................. A61N 1/36046
See application file for complete search history.

(56) References Cited

U.S. PATENT DOCUMENTS

| | | | | |
|---|---|---|---|---|
| 2012/0212820 A1* | 8/2012 | Jiang | ..................... | C23C 14/028 |
| | | | | 359/566 |
| 2015/0182748 A1* | 7/2015 | Gefen | ................ | G02B 27/0172 |
| | | | | 607/54 |

FOREIGN PATENT DOCUMENTS

| | | | | |
|---|---|---|---|---|
| DE | 10315397 A1 | 10/2004 | | |
| WO | WO-2010062481 A | * 6/2010 | ............. | G02C 11/10 |

* cited by examiner

Primary Examiner — Gary Jackson
Assistant Examiner — Anant A Gupta
(74) Attorney, Agent, or Firm — Murphy, Bilak & Homiller, PLLC (57) ABSTRACT

A device and a method, by means of which energy can be supplied to a retinal implant (12) via infrared radiation, are provided. To this end, infrared light is coupled in from an infrared light source (14), for example into a spectacle lens (13), and coupled out toward an eye (10) by way of an output coupling device (17) in order to illuminate the retinal implant (12).

5 Claims, 8 Drawing Sheets

DEVICE AND METHOD FOR SUPPLYING ENERGY TO AN ACTIVE OCULAR IMPLANT

TECHNICAL FIELD

The present application relates to devices and methods for supplying energy to an active ocular implant by means of infrared radiation.

BACKGROUND

Active ocular implants are devices which are implanted into an eye of a patient in order to carry out certain functions there. Retinal implants are examples of such active ocular implants. Retinal implants have been developed to restore vision, at least to a certain degree, for persons who have lost the ability to see but who still have a connection from the optic nerve to the brain. Such retinal implants usually comprise an image sensor which produces—optionally with additional circuits—electric pulses that are then registered via the optic nerve.

Other examples of active ocular implants are actively accommodating intraocular lenses or implanted sensors for measuring parameters in the eye, for example the blood sugar level in the aqueous humor. In contrast to passive implants (e.g., simple lenses), such active ocular implants require electric energy in order to be operated.

One option for the energy supply lies in the supply of infrared radiation below the visible range, which is then converted into electric energy by the active ocular implant, essentially by means of a solar cell or a similar device.

Figure 13A:
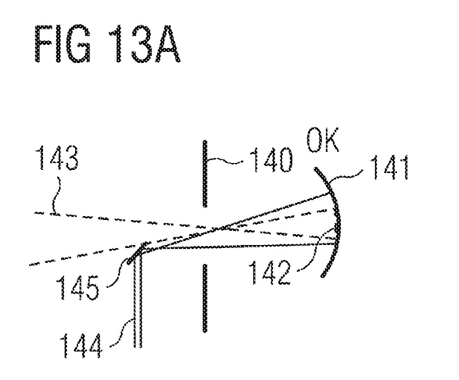
FIGS. 13A and 13B show diagrams for elucidating a conventional procedure.
Figure 13B:
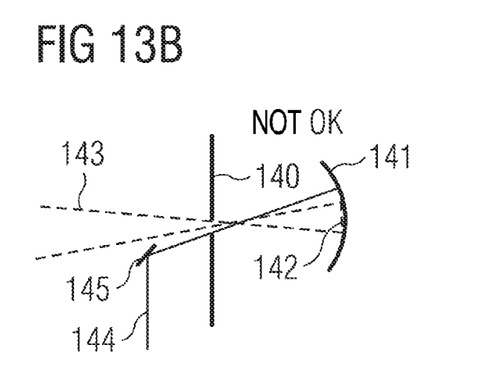

In a conventional approach, this is effected by virtue of infrared radiation being coupled slightly obliquely into the eye from an infrared light source, e.g., an infrared laser, via a deflection element such as a prism or a mirror. This is depicted in FIGS. 13A and 13B. In FIGS. 13A and 13B, an infrared beam 144 is steered via a deflection element 145, e.g., a prism, through an iris diaphragm 140 of an eye 141. By way of example, such a deflection element 145 can be arranged at an edge of a spectacle lens of corresponding spectacles. Beams (e.g., visible light) are denoted by 143, said beams corresponding to a principal viewing direction of the eye, for example an optical axis when looking straight ahead.

Should the iris diaphragm 140 be open wide enough, as shown in FIG. 13A, the infrared beam 144 is incident in the region of a retinal implant 142, which serves here as an example of an active ocular implant and which is situated in the eye 141, and consequently said retinal implant can be supplied with energy. However, if, as shown in FIG. 13B, the iris diaphragm 140 narrows, i.e., is closed, the infrared beam reaches into the eye next to the implant 142, and so the implant can no longer be supplied with energy. Furthermore, changing the viewing direction may lead to the infrared beam being shadowed by the iris, particularly if the latter is narrowed.

Consequently, it may be necessary in this conventional approach to enlarge the iris diaphragm by operation, necessitating an additional surgical intervention, e.g., when inserting the implant 142, or even an additional operation. Furthermore, the permanent enlargement of the iris has a negative effect on the capability of the eye of adapting to different light conditions and on the aesthetic result of the surgery.

Therefore, it is an object of the present invention to provide devices and methods for supplying an active ocular implant with energy, which are also functional in the case of comparatively small iris diaphragms and/or in the case of varying viewing directions.

SUMMARY

According to a first aspect, a device for supplying energy to an active ocular implant, e.g., a retinal implant, is provided, comprising:
an infrared light source,
a spectacle lens, wherein the infrared light source is arranged in such a way that light emanating from the infrared light source reaches a steering device arranged in or on the spectacle lens, said steering device steering the infrared light toward an eye of a user.

The arrangement of the steering device renders it possible to determine the direction from which the infrared light is incident on the eye.

To this end, in particular, the infrared light can be coupled into the spectacle lens, the latter then acting as a waveguide for steering the infrared light to the steering device. The latter then acts as an output coupling device and couples out the light toward the eye.

By coupling the infrared radiation into the spectacle lens and by providing the output coupling element, it is possible to flexibly choose the direction from which the infrared light is incident on the eye, in contrast to the oblique input coupling from the prior art. Moreover, an advantage arising over free-beam optics is that the light guidance in the spectacle lens renders it possible to avoid shadowing by cheekbones, eyelashes, eyebrows, hair and the like.

The steering device may be transparent to visible light in order thus to facilitate an unimpeded view.

Preferably, the infrared light source substantially emits only (i.e., for example, apart from unwanted effects, e.g., incomplete filtering) in the infrared region above 780 nm so as not to interfere with the perception of visible light.

The steering device can be configured to steer the infrared light toward the eye, e.g., to couple said infrared light out of the spectacle lens, in a manner at least partly coaxial to a viewing direction of the eye.

The supply of the active ocular implant can be ensured by the coaxial input coupling, even in the case of a small iris.

The steering device can be configured to steer the infrared light toward the eye, e.g., to couple said infrared light out of the spectacle lens, as a plurality of beams with different directions.

By using a plurality of directions, a supply of energy to the active ocular implant can be ensured, even in the case of eye movements. This is also an advantage over free-beam optics with a deflection or the like at a position, in which only one direction is produced.

The steering device can be configured to steer the infrared light toward the eye, e.g., to couple said infrared light out, as one or more focused beams.

One or more foci of the one or more beams can lie near a pupil of the eye (defined by an iris diaphragm).

In another embodiment, one or more foci of the one or more beams can lie near the center of rotation/eye center point of the eye. Here, the center of rotation is a point about which the eye rotates.

Within the scope of this application, "near" may mean a region of ±5 mm, ±4 mm, ±3 mm, ±2 mm or ±1 mm from the respective point or location (pupil or center of rotation/eye center point).

The steering device can comprise a transmission grating, a reflection grating, a partly transmissive beam splitter, a wavelength-selective beam splitter, a volume hologram and/or a Fresnel element.

Output coupling can be effected in a comparatively simple manner by way of a Fresnel element or an optical grating, or else by way of a wavelength-selective beam splitter, without there being a substantial impediment to the view through the spectacle lens.

The transmission grating and/or the reflection grating may comprise a holographic grating.

According to a second aspect, a method is provided, comprising:
steering infrared light to a steering device in or on a spectacle lens and
steering the infrared light from the steering device toward an eye of a user.

In particular, the method can be realized by coupling infrared light into a spectacle lens and coupling the infrared light out toward an eye of a user.

The steering or output coupling can comprise steering or output coupling at different points of the spectacle lens at different angles toward the eye.

The steering or output coupling can comprise steering or output coupling as one or more beams with a focus near a pupil of the eye in each case.

The steering or output coupling can comprise steering or output coupling as one or more beams with a focus near the center of rotation of the eye in each case.

The method may be carried out with one of the above-described devices.

BRIEF DESCRIPTION OF THE DRAWINGS

Below, the invention will be explained in detail by way of embodiments, with reference being made to the attached drawing. In the Figures.

DETAILED DESCRIPTION

Various embodiments are explained in detail below. These embodiments serve merely for illustration and should not be interpreted as restrictive. By way of example, a description of an embodiment with a plurality of elements or components should not be interpreted to the effect that all these elements or components are necessary for implementation purposes. Rather, other embodiments also may contain alternative elements or components, fewer elements or components or else additional elements or components. Elements or components of different embodiments can be combined with one another, unless indicated otherwise. Modifications and developments which are described for one of the embodiments may also be applicable to other embodiments.

In order to avoid repetition, the same elements or corresponding elements in the various Figures are denoted by the same reference sign and are not explained a number of times.

A retinal implant is used in the following embodiments as an example of an active ocular implant. However, the techniques described are also applicable to other active ocular implants, for example the ocular implants mentioned at the outset.

Figure 1:
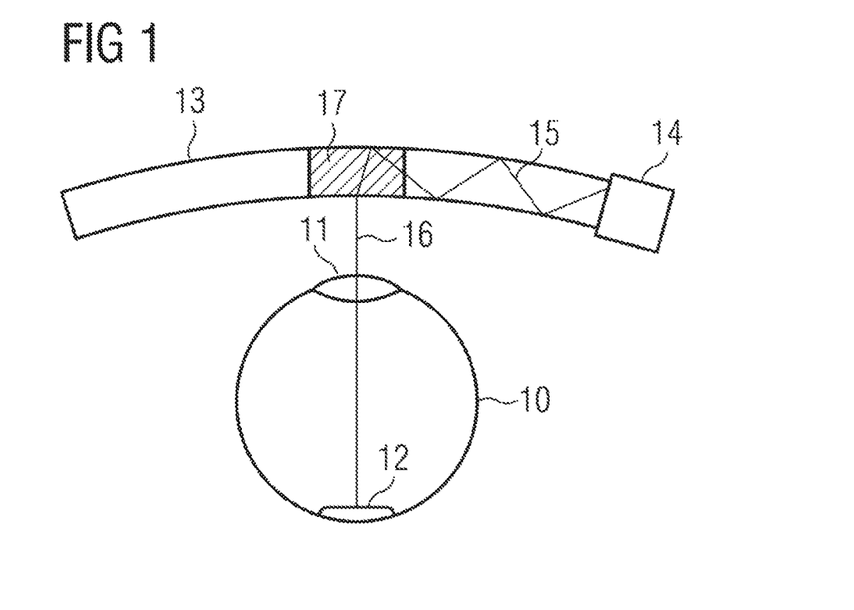
FIG. 1 shows a schematic cross-sectional view of a device according to an embodiment.

FIG. 1 schematically illustrates a device according to an embodiment. Here, the device of the embodiment in FIG. 1 serves to supply energy to a retinal implant 12 in an eye 10 of a user by means of infrared radiation. Then, this infrared radiation can be converted into electric energy by the retinal implant 12 using a solar cell or the like.

The device in FIG. 1 comprises a spectacle lens 13, which should be arranged in front of the eye 10. Here, within the scope of the present invention, a spectacle lens is understood to mean, in general, a transparent medium which can be arranged in front of the eye 10 by means of an appropriate holder. Such a spectacle lens 13 may consist of a glass or else of a plastics material. The spectacle lens may have an embodiment with a curvature along one or two directions, or else it may be planar. The spectacle lens may have optical refractive power. Furthermore, the device in FIG. 1 comprises an infrared light source 14. By way of example, an infrared light-emitting diode (LED; or a plurality of LEDs) can be used as an infrared light source 14; however, use can also be made of other suitable light sources, possibly in conjunction with filters for filtering out visible light. Preferably, the infrared light source 14 emits substantially only infrared light (optionally by the use of appropriate filters) and emits substantially no light in the visible range in order not to interfere with a perception of the surroundings implemented by means of the retinal implant 12. In particular, the infrared light source 14 can comprise an infrared laser. An infrared laser, for example an infrared semiconductor laser diode, has a particularly narrow bandwidth in respect of the emitted light, which may aid the function of the steering device. When using a filter, "substantially" may mean "within the quality of the filter". Here, the wavelength of the infrared light may lie above 780 nm, in particular. The infrared light 15, which is emitted by the infrared light source 14, may be monochromatic, i.e., substantially have only one wavelength, or else it may have a broader spectral distribution, for example of the order of approximately 30 nm.

Here, the infrared light 15 is coupled into the spectacle lens 13 in such a way that the spectacle lens 13 serves as a waveguide for the infrared light. Such a wave guidance is carried out substantially by total-internal reflection at the inner surfaces of the spectacle lens 13, for the purposes of which the input coupling angle of the infrared light 15 should be chosen accordingly in order to satisfy the condition for total-internal reflection. If the condition is not satisfied, there are high losses of infrared light. Optionally, a beam shaping optical unit can be arranged between the infrared light source 14 and the spectacle lens 13 in order to suitably shape, e.g., collimate, the light emitted by the light source before it is coupled into the spectacle lens. Moreover, the beam shaping optical unit may contain further optical elements such as waveplates or diffusers.

Moreover, the device in FIG. 1 comprises an output coupling device 17 (an example of a steering device), which is arranged in the spectacle lens 13 and which couples out the infrared light 15 as output coupled light 16 in a direction toward a pupil 11 of the eye. Here, the output coupling device 17 is wavelength-selective, and so the infrared light is coupled out but the corresponding region of the spectacle lens 13, in which the output coupling device 17 is arranged, remains transparent in the visible spectrum such that the retinal implant 12 can record the image impression of the observed surroundings without interference.

Here, output coupling is preferably effected in such a way that at least some of the output coupled light 16 lies coaxially with the viewing direction of the eye 10, i.e., with the optical axis of the eye 10 in the viewing direction. This may be the case, in particular, for a principal viewing direction (e.g., looking straight ahead). Preferably, as will still be explained in more detail below, the output coupling is effected in such a way that the implant is illuminated and hence it remains active for a viewing angle range of the eye 10 that is as large as possible. Here, the output coupling device 17 can be realized in various ways. By way of example, use can be made of an optical grating, in particular an optical grating in reflection on a surface of the spectacle lens 13 facing away from the eye 10, an optical grating in transmission on a side of the spectacle lens 13 facing the eye 10, a wavelength-selective mirrored Fresnel structure or a conventional wavelength-specific beam splitter, e.g., a conventional dichroic beam splitter. Combinations thereof are also possible. The output coupling device in the form of a Fresnel structure, an optical grating in transmission or an optical grating in reflection may be arranged in the interior of the spectacle lens in some embodiments (for example, for protecting this output coupling device from damage or dirt).

By output coupling coaxial to a viewing direction of the eye, like in FIG. 1, an illumination and hence an energy supply of the retinal implant 12 can be ensured even in the case of a comparatively small iris aperture, in contrast to the conventional approaches explained in the introduction with reference to FIG. 13. This is elucidated with reference to FIGS. 2A and 2B, which are similar to FIGS. 13A and 13B.

Figure 2A:
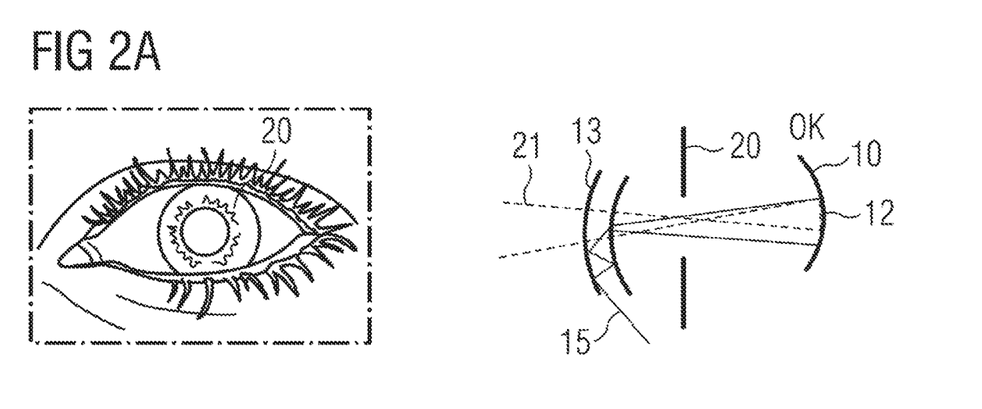
FIGS. 2A and 2B show illustrations for elucidating advantages of the embodiment of FIG. 1.
Figure 2B:
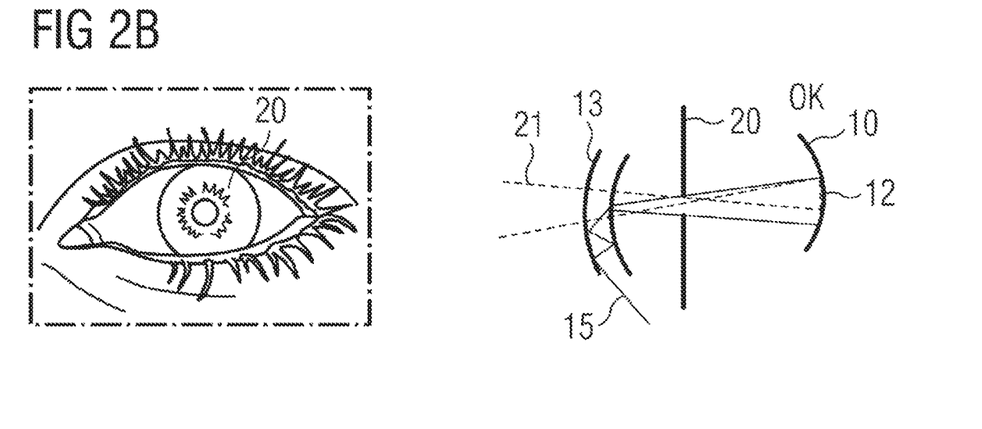

FIG. 2A illustrates the situation for the eye 10 with a relatively wide-open iris 20. FIG. 2B illustrates a situation for an iris 20 that is closed further. In both cases, both the infrared light 15 and visible light 21 from the surroundings reaches the retinal implant 12 in the eye 10.

Consequently, the using embodiment illustrated in FIG. 1, it is possible to avoid, for example, a surgical opening of the iris diaphragm in order to sufficiently supply energy to the retinal implant 12.

As already explained, the infrared light is preferably coupled out of the spectacle lens in such a way that the implant is illuminated for a viewing angle range that is as large as possible, for example from different locations or from a broader range. This is now explained in more detail with reference to FIGS. 3-5.

If objects are observed in different directions, the eye moves and there is a change in the viewing direction and the optical axis of the eye. This is illustrated schematically in FIG. 3. In a first viewing direction that corresponds to a dashed line 30, the implant is situated in a position 12. If the eye moves in a rotational movement corresponding to an arrow 32, the implant may come to rest, for example, as illustrated as 12', corresponding to a viewing direction 31. By way of appropriate output coupling, it is possible to ensure that the retinal plant is sufficiently illuminated by infrared light in both positions in order to be supplied with energy.

Figure 4:
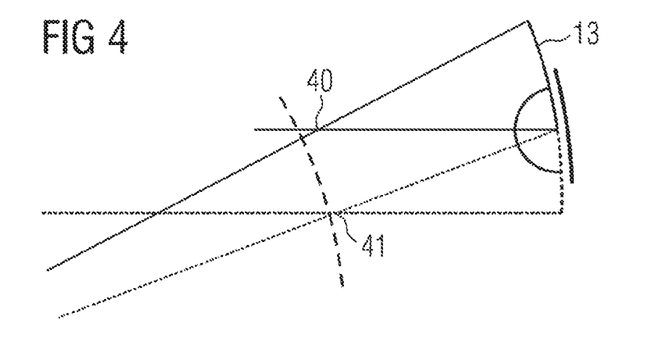
FIG. 4 shows a schematic illustration for elucidating input coupling from different directions.

Here, FIG. 4 shows an example with two different output coupling directions from a spectacle lens 13. In particular, the spectacle lens in FIG. 4 has, as an example, two zones, from which light is coupled out corresponding to two different viewing directions. This leads to two different foci (focal points) 40, 41, which preferably lie close to the iris diaphragm such that a passage is facilitated, even through an iris diaphragm (i.e., the pupil defined by the iris diaphragm) that is closed comparatively far.

Typically, a retinal implant has a width of 4-8 mm for example, and a pupil diameter in the case of light adaptation, i.e., an iris that is closed relatively far, may be 2-3 mm. Consequently, it is preferable for a focus of the output coupling, like the points 40 and 41 in FIG. 4, to lie near the iris since no complete illumination of the implant would be possible by a collimated beam (also referred to as illumination beam) with the diameter of the pupil, and there would be too great shadowing by the iris in the case of the beam focused on the center point of the eye (point of rotation of the eye), for example, wherein the center point of the eye has the same distance from the implant and the iris. This, in preferred embodiments, use is made of a divergent beam path that is focused closely in front of or behind the iris (e.g., focused in the region of ±5 mm, ±4 mm, ±3 mm, ±2 mm or ±1 mm around the iris) or a plurality of such beam paths. Here, the focus or foci preferably lie approximately 13-30 mm from a surface of the spectacle lens facing the eye, corresponding to typical distances between spectacle lens and iris in the range of 16-27 mm. Other values are likewise possible.

In other embodiments, it is also possible to focus on to or near to the center point of the eye, e.g., in a region of ±5 mm, ±4 mm, ±3 mm, ±2 mm or ±1 mm in front of or behind the center point of the eye. Although, as explained above, this may lead to shadowing, this can obtain a higher tolerance in relation to, e.g., lateral displacements of the eye in relation to the illumination beam. Which option is selected (focusing near the pupil/iris or near the center point of the eye), may be chosen depending on the conditions of the respective implementation and the respective eye implant, e.g., depending on an energy requirement of the eye implant or limit values for the energy of the illumination beam to be observed.

While FIG. 4 only illustrates two beam paths of this kind, use can be made of a plurality of such beam paths. An example to this end is shown in FIG. 5. Here, FIG. 5A shows a schematic plan view of a spectacle lens 13 and FIG. 5B shows a cross-sectional view along a line A-A in FIG. 5A.

Figure 5A:
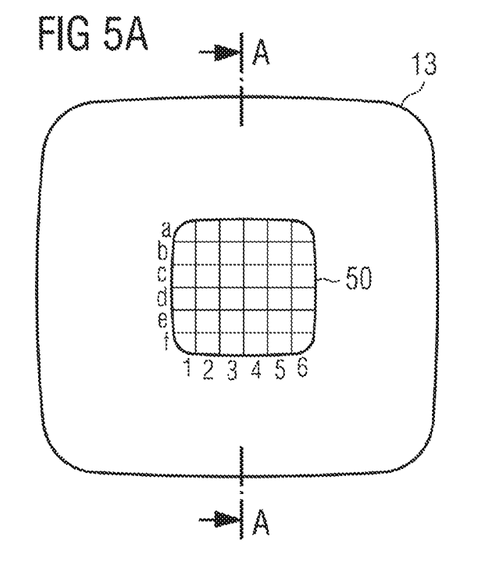
FIG. 5A shows a plan view of a spectacle lens according to an embodiment.
Figure 5B:
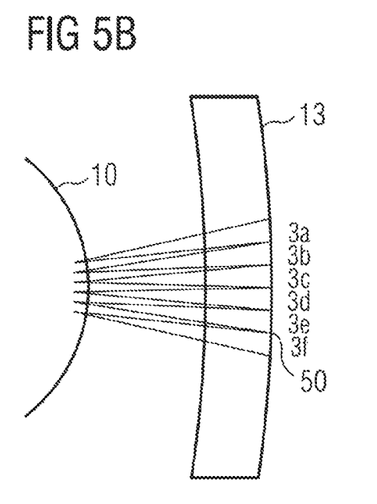
FIG. 5B shows a cross-sectional view of FIG. 5A along a line A-A.

Here, the spectacle lens 13 in FIGS. 5A and 5B has an arrangement of 36 output coupling elements, which are arranged in a 6×6 matrix 50 and consequently form the output coupling device 17 of FIG. 1. Each of the output coupling elements of the matrix 50 produces a beam which, as explained above, preferably has a focus near the pupil or iris. Light is steered toward the eye 10 from a different angle from each of the output coupling elements, and so the implant 12 can be illuminated in various viewing directions. While FIGS. 5A and 5B illustrate a 6×6 matrix of output coupling elements, this should only be understood to be exemplary and any arrangement can be used, depending on space on the spectacle lens and available IR light.

Essentially, there can be a transition to continuous output coupling over a certain region, in which infrared light is coupled out in a certain angle range from each point of the spectacle lens surface. Here, this angle is preferably chosen in such a way that as little light which cannot reach the retinal implant in any position of the eye 10 as possible is output coupled in order to keep losses as low as possible and in order to restrict a total amount of required light energy. In this way, the service life of a power supply (e.g., battery) for the infrared light source can be increased and the operational reliability of the spectacles can be increased since lower powers are required.

Such output coupling into a defined angle range can be achieved, for example, by varying a grating constant of an output-coupling grating. Another option lies in a polychromatic illumination of a grating with an unchanging grating constant, wherein the angle changes depending on the wavelength of the light. By way of example, such a polychromatic illumination can have a spectral width of the order of 30 nm, although it is not restricted thereto.

Another option lies in a curvature of output coupling surfaces of a Fresnel structure used as an output coupling device, said Fresnel structure, in particular, being able to be mirrored in a wavelength-selective manner and/or filled with optical medium (e.g., of the spectacle lens). Combinations of these approaches are also possible.

Next, two embodiments of devices according to the invention will be explained in yet more detail with reference to FIGS. 6 and 7.

Figure 6:
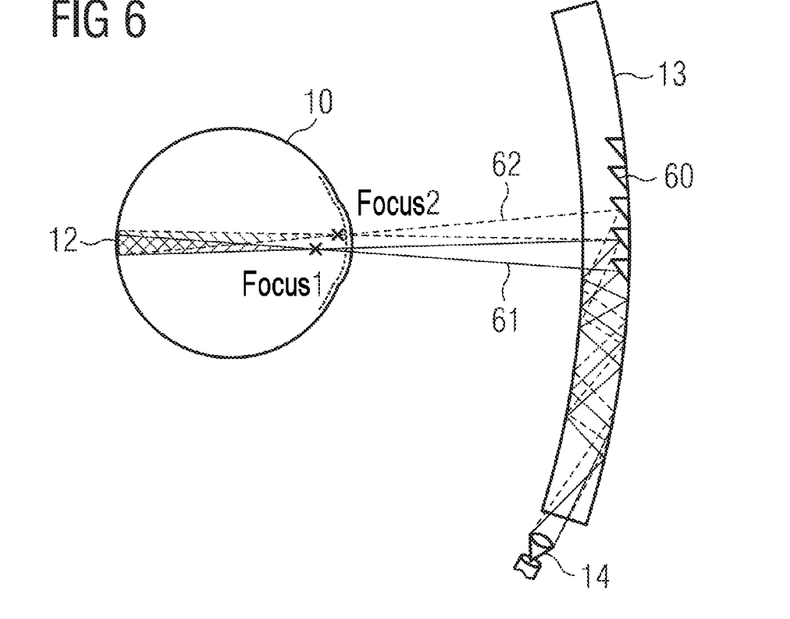
FIG. 6 shows a cross-sectional view of a device according to an embodiment.

By way of example, in the embodiment of FIG. 6, the infrared light source 14 comprises one or more infrared light-emitting diodes, which produce a polychromatic infrared light beam, for example with a full width at half maximum (FWHM) of 30 nm. However, other light sources may also be used. As an output coupling device, the device in FIG. 6 comprises a Fresnel element 60, wherein various facets of the Fresnel element can produce light beams with different foci near an iris in order to illuminate the retinal implant 12, in particular at different eye positions. The facets of the Fresnel element may be mirrored in a wavelength-selective manner. The Fresnel element 60 can be filled with the material of the spectacle lens 13. As an example, a first light beam 31 with a first focus (focus 1) and a second light beam 62 with a second focus (focus 2) are plotted, wherein further facets can produce further beams. The facets of the Fresnel element 60 can be slightly curved in this case in order to produce beams with the desired focus. Here, the light produced by the light source 14 is slightly divergent.

Figure 7:
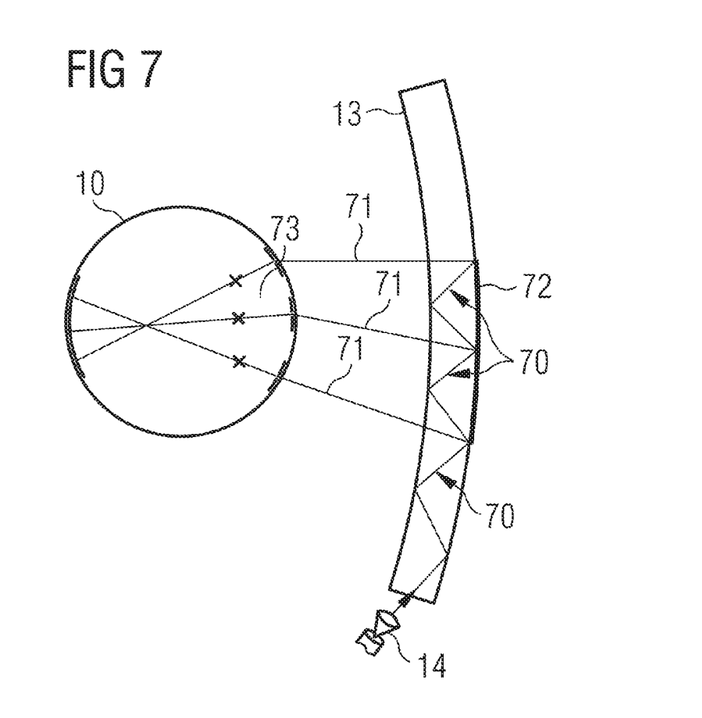
FIG. 7 shows a cross-sectional view of a device according to a further embodiment.

FIG. 7 illustrates a further embodiment. In the embodiment of FIG. 7, a grating 70 (a reflection grating), which, in particular, may be implemented as a holographic grating, is arranged at a surface of the spectacle lens 13 facing away from the eye. Here, beams are produced as the first order output couplings 71 by the reflection hologram 72, while an output coupling of zeroth order denoted by 70 propagates further in the spectacle lens 13, as a result of which output coupling can be achieved over a greater angle range. Foci of the light beams, which may again lie near an iris or pupil, are denoted by 73.

In other embodiments, an optical element, e.g. a volume hologram exposed in a film, may be applied to the spectacle lens as an output coupling element, for example laminated onto said spectacle lens or else enclosed below the surface in the interior of the spectacle lens in order to provide protection from ambient influences. Here, the volume hologram is arranged substantially parallel to at least one surface of the spectacle lens.

Figure 8:
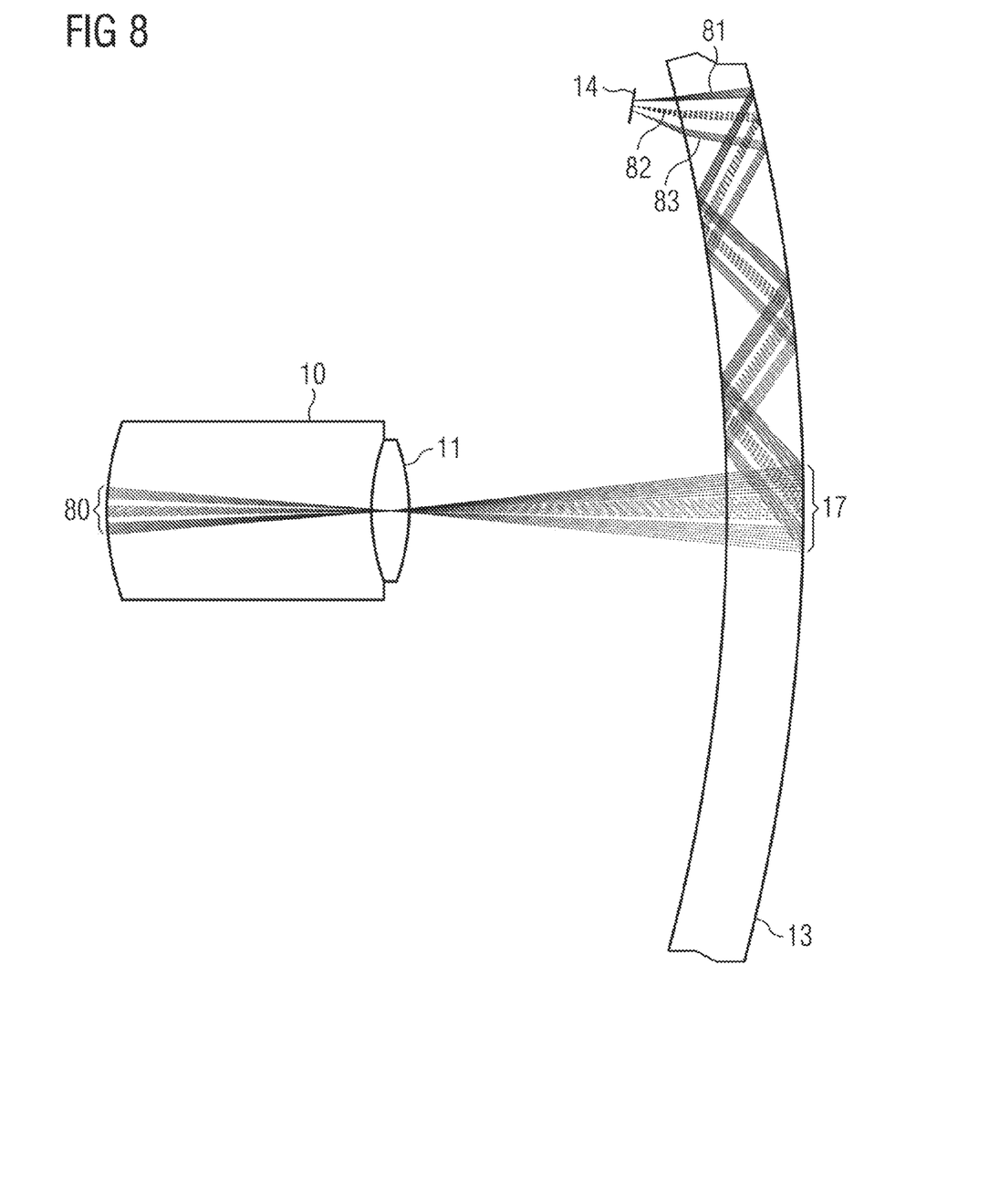
FIGS. 8-10 show different views of a device according to an embodiment with different eye positions.
Figure 9:
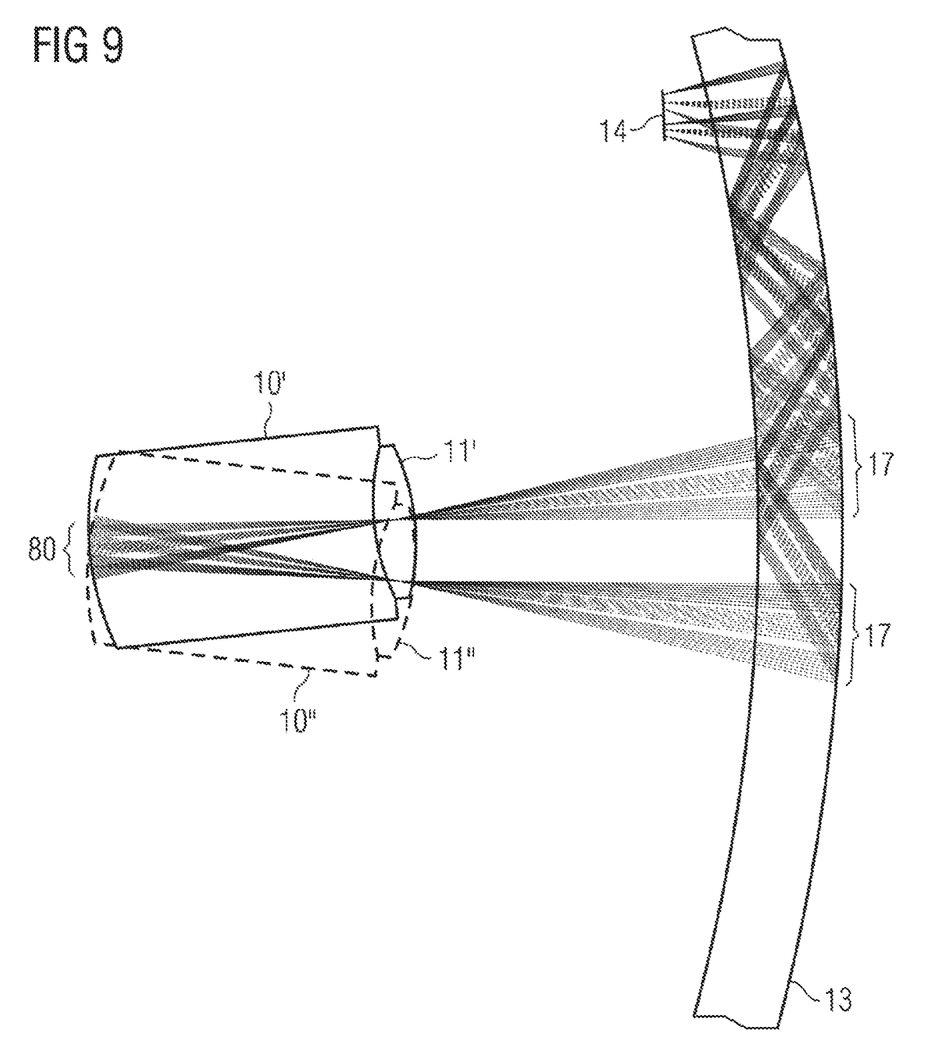
Figure 10:
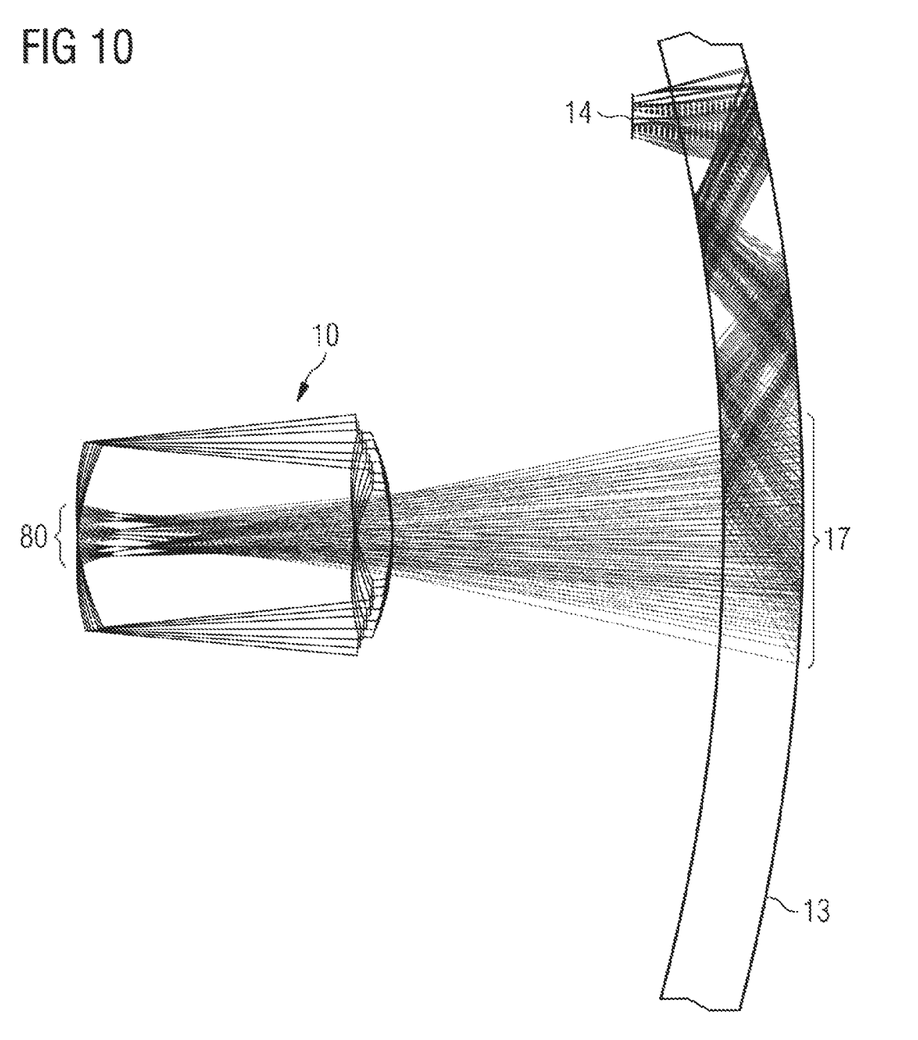

A further embodiment, in which a grating is likewise used, is illustrated in the embodiments 8-10. Here, a coupling element 17, which is embodied as a reflection grating, is arranged in a spectacle lens 13 on a side facing away from an eye 10. 80 denotes a region in which, in the case of a respective position of the eye 10 or in the respective illustrated positions, a back wall of the eye, where a retinal implant may be arranged, is illuminated.

FIG. 8 illustrates a situation in which the eye 10 looks "straight ahead". A light source 14 produces infrared light, of which three beams 81, 82, 83 are illustrated as an example, said light beams emanating from different parts of the illumination device 14 and/or being able to represent different parts of a divergent beam emanating from the IR light source 14.

In FIG. 9, two extreme positions 10', 10" of the eye 10 with corresponding positions of the pupil 11', 11" are illustrated. Moreover, corresponding light beams are illustrated, said light beams emanating from the infrared light source 14 and being steered by corresponding regions of the output coupling device 17 into a region 18 on the back wall of the eye. Finally, FIG. 10 shows a plurality of positions of the eye 10 and a substantially entire region of the output coupling device 17.

In the embodiments discussed with reference to FIGS. 1-9, light is coupled into a spectacle lens. Free-beam optics can be used in other embodiments. A corresponding embodiment is illustrated in FIG. 14.

Figure 3:
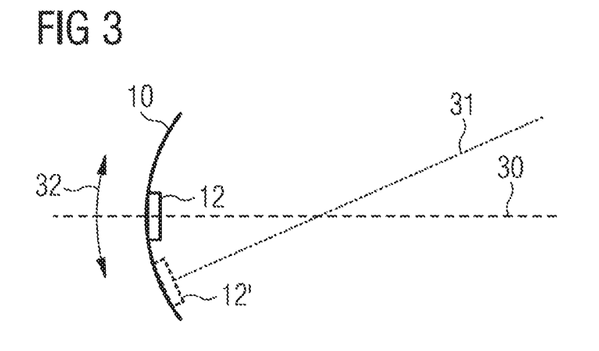
FIG. 3 shows an illustration for elucidating an eye movement.
Figure 14:
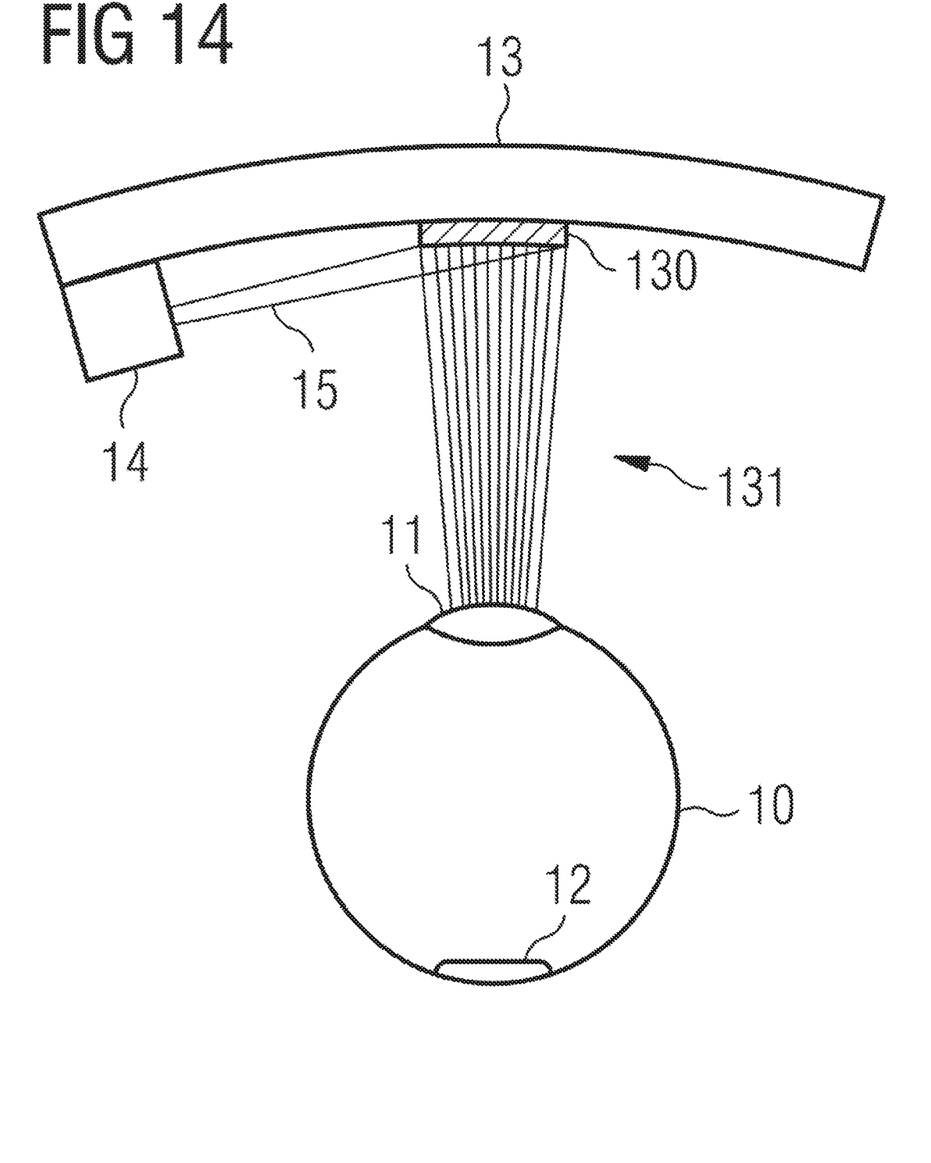
FIG. 14 shows a cross-sectional view of a device according to a further embodiment.

In FIG. 14, infrared light from an infrared light source 14 reaches, as a free beam, a guiding device 130 that has been applied onto or worked into an inner side of a spectacle lens 13. The guiding device 130 is preferably transparent to visible light. As discussed with reference to FIGS. 3-5, in particular, the steering device 130 steers the infrared light to the eye 10 as a plurality of beams 131. As already discussed above, this can be carried out by means of a grating (in particular, a reflection grating and/or a holographic grating) or a Fresnel element. The explanations and details which were provided for corresponding output coupling for the purposes of taking account of an eye movement above, e.g. with reference to FIGS. 3-5, are also applicable to the embodiment of FIG. 14.

Figure 11:
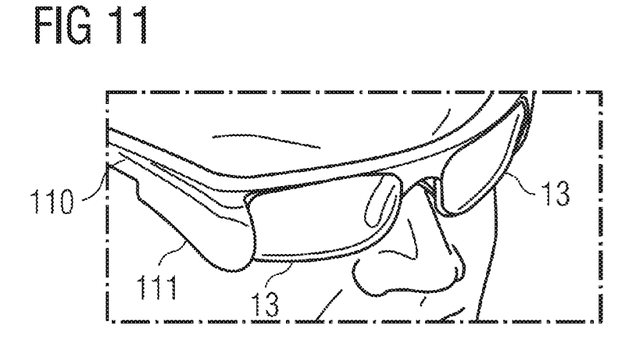
FIG. 11 shows a view of spectacles according to an embodiment.

FIG. 11 illustrates a pair of spectacles 110 according to an embodiment. The pair of spectacles 110 may have one or two spectacle lenses 13, as discussed above with reference to FIGS. 1-10 and 14. If a retinal implant that needs to be supplied with energy is only present in one eye, a corresponding spectacle lens 13 is only required on the corresponding side. Here, an infrared light source like the infrared light source 14 can be housed in a region 111.

Figure 12:
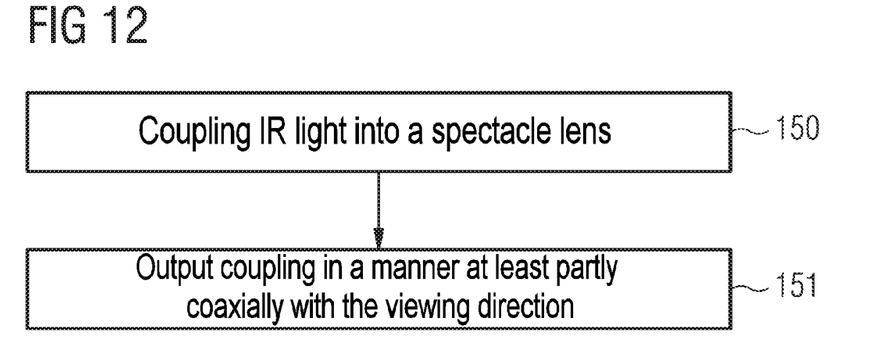
FIG. 12 shows a flowchart for elucidating a method according to an embodiment.

FIG. 12 shows a flowchart for elucidating a method according to an embodiment. The method in FIG. 12 can be implemented, in particular, by means of the devices discussed with reference to FIGS. 1-11 and details that were discussed with reference to the devices can also be applied to the method in FIG. 12.

Infrared light is coupled into a spectacle lens in a step 150 in FIG. 12. By way of example, as described above, the infrared light can be produced by an infrared light source or any other suitable light source, using filters where necessary. Then, in step 151, the light is output coupled at least partly coaxially with a viewing direction of an eye, i.e., partly coaxially with an optical axis of the eye. Partly coaxially means, in particular, that a different part of the output coupled light can lie coaxially with the viewing direction, depending on the viewing direction. Here, as described, output coupling can be brought about, in particular, in such a way that foci of beams of output coupled light lie near a pupil of the eye.

As already described above, the above embodiments serve merely for illustration and should not be interpreted as restrictive.

What is claimed is:

1. A device configured to illuminate at least a portion of the retina of an eye of a user of the device with divergent infrared light, for supplying energy to a retinal implant, the device comprising:
    an infrared light source to output the infrared light,
    a spectacle lens,
    a steering device arranged in or on the spectacle lens,
    wherein the infrared light source is arranged in such a way that the infrared light reaches the steering device,
    wherein the steering device focuses the infrared light toward the eye of the user as one or more focused beams, and wherein one or more foci of the one or more beams lie near a pupil of the eye, where "near" denotes a region of +/−5 millimeters, such that the one or more beams are divergent at the retina.

2. The device as claimed in claim 1, wherein the steering device comprises at least one of a transmission grating, a reflection grating, a wavelength-selective beam splitter, a volume hologram or a Fresnel element.

3. The device as claimed in claim 2, wherein at least one of the transmission grating or the reflection grating comprises a holographic grating.

4. The device of claim 1, wherein the one or more focused beams comprise multiple focused beams corresponding to multiple viewing directions of the eye, with the foci of each focused beam lying near the pupil of the eye, for the corresponding viewing direction of the eye.

5. A method of supplying energy to a retinal implant, the method comprising:
    directing infrared light into a steering device arranged in or on a lens of spectacles worn by a user, the lens being positioned in front of an eye of the user that has the retinal implant; and
    redirecting the infrared light from the steering device toward the eye of the user as one or more focused beams, and wherein one or more foci of the one or more beams lie near a pupil of the eye, where "near" denotes a region of +/−5 millimeters, such that the one or more beams are divergent at the retina, thus supplying the retinal implant with energy.

* * * * *

UNITED STATES PATENT AND TRADEMARK OFFICE
CERTIFICATE OF CORRECTION

PATENT NO. : 11,253,702 B2
APPLICATION NO. : 16/079226
DATED : February 22, 2022
INVENTOR(S) : J. Kindt et al.

It is certified that error appears in the above-identified patent and that said Letters Patent is hereby corrected as shown below:

In the Specification

Column 5, Line 53, please change "the using embodiment" to -- using the embodiment --

Column 7, Line 46, please change "beam 31" to -- beam 61 --

Column 8, Line 24, please change "region 18" to -- region 80 --

Signed and Sealed this
Seventeenth Day of May, 2022

Katherine Kelly Vidal
*Director of the United States Patent and Trademark Office*